United States Patent [19]
Peifer et al.

[11] Patent Number: 5,830,958
[45] Date of Patent: Nov. 3, 1998

[54] POLYNUCLEAR METALLOCENE PREPARATION AND USE

[75] Inventors: Bernd Peifer; Helmut G. Alt, both of Bayreuth, Germany; M. Bruce Welch, Bartlesville, Okla.

[73] Assignee: Phillips Petroleum Company, Bartlesville, Okla.

[21] Appl. No.: 439,684

[22] Filed: May 12, 1995

[51] Int. Cl.$^6$ .............................. C08F 4/06; C08F 4/72; C08F 4/44; C07F 9/00

[52] U.S. Cl. .................. 526/113; 526/114; 526/118; 526/119; 526/904; 526/943; 556/43; 556/53; 556/58

[58] Field of Search ................ 596/11, 20, 43, 596/53, 58, 87, 113, 118, 943; 534/10, 15

[56] References Cited

U.S. PATENT DOCUMENTS

| | | | |
|---|---|---|---|
| 4,147,709 | 4/1979 | Lynch | 260/429.3 |
| 4,530,914 | 7/1985 | Ewen et al. | 526/943 |
| 5,319,790 | 6/1994 | Rohrmann et al. | 556/28 |
| 5,449,651 | 9/1995 | Reddy et al. | 556/11 |

FOREIGN PATENT DOCUMENTS

| | | | |
|---|---|---|---|
| 650554 | 2/1993 | Australia | 556/11 |
| 0 577 581 | 1/1994 | European Pat. Off. . | |
| 0 582 194 | 2/1994 | European Pat. Off. | 556/11 |

OTHER PUBLICATIONS

J. Gautier et al., No. 262.–Derives acetyleniques du fluorene: synthese et description des fluorenylalcynes (1er memoire), Memoires Presentes a la Societe Chimique, pp. 1735–1740, 1965.

A. Hubert et al., "Base–catalysed Prototropic Isomerisations. Part II. The Isomerisation of N–Prop–2–ynyl Heterocycles into N–Substituted Allenes and Acetylenes", J. Chem. Soc. (C), pp. 606–608, 1968.

M. Fessler et al., "nido–Carborane Building–Block Reagents. 1. Polycyclic Arene RR'C2B4H6 Derivatives: Synthesis via Indenyl and Fluorenyl Alkynes and Metal–Promoted Oxidative Fusion", Inorg. Chem., vol. 7, pp. 3069–3075, 1988.

Angew. Chem. Int. Ed. Engl.,vol. 15, No. 6, pp. 333–340 (1976), Schwartz et al.

Primary Examiner—Glenn A. Caldarola
Assistant Examiner—J. Pasterczyk
Attorney, Agent, or Firm—Edward L. Bowman

[57] ABSTRACT

A process for preparing polynuclear metallocenes by reacting a metallocene in which one of the cyclopentadienyl-containing radicals has a substituent having olefinic or acetylenic unsaturation with a second metallocene having a metal which comes from groups IVb to VIb of the periodic table and a metal-hydride bond. The use of the resulting metallocenes in the polymerization of olefins is disclosed, including techniques for using such metallocenes to produce solid prepolymerized metallocene-containing catalyst systems suitable for use in the polymerization of olefins.

20 Claims, No Drawings

POLYNUCLEAR METALLOCENE PREPARATION AND USE

FIELD OF THE INVENTION

This invention relates to metallocenes. In another aspect this invention relates to polynuclear metallocenes. In still another aspect this invention relates to the use of polynuclear metallocenes in the polymerization of olefinically unsaturated monomers.

BACKGROUND OF THE INVENTION

The term "Metallocene" as used herein refers to a derivative of cyclopentadienylidene which is a metal derivative containing at least one cyclopentadienyl component which is bonded to a transition metal. The transition metal is selected from Groups IVB, VB, and VIB, preferably IVB and VIB. Examples include titanium, zirconium, hafnium, chromium, vanadium, as well as rare earth metals. A number of metallocenes have been found to be useful for the polymerization of olefins. Generally, the more preferred catalysts are metallocenes of Zr, Hf, or Ti. The term "polynuclear metallocene" as used herein refers to an organometallic compound containing at least two transition metals each of which is bonded to at least one different cyclopentadienyl-containing group.

One of the advantages of metallocenes in polymerization has been the fact that they often appear to be "single-site" catalysts that give a very narrow range of molecular weight polymers of very similar molecular structure. This often leads to narrow molecular weight distributions. The resulting polymers of narrow molecular weight distribution have some advantages over polymers having broader molecular weight distribution in some application; however, they sometimes have disadvantages in other applications.

One object of the present invention is provide a new type of metallocene having at least two metal centers.

Another object of the present invention is to provide a method for polymerizing olefins that can lead to broader molecular weight distributions.

Still another object of the present invention is to provide a method for forming a solid metallocene catalyst system suitable for use in particle form polymerizations. Other aspects, objects, and advantages of the present invention will be apparent from the following disclosure.

SUMMARY OF THE INVENTION

In accordance with the present invention there is provided a process for forming a polynuclear metallocene comprising reacting a first metallocene of the formula

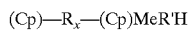

with a second metallocene, wherein said second metallocene has at least one cyclopentadienyl-containing group having a substituent having an olefinic or acetylenic function and wherein in the first metallocene each Cp is the same or different cyclopentadienyl-containing group, R is an organic moiety connecting the two Cp groups; Me is a transition metal, R' is selected from the group consisting of hydrocarbyl, hydrocarbyloxy and halide radicals; and x is 1 or 0. The metals of the first and second metallocenes can be the same or different. In accordance with another aspect of the present invention the resulting polynuclear metallocene is used as a catalyst in the polymerization of olefins. In an especially preferred embodiment the polynuclear metallocene is used to prepare a solid prepolymerized catalyst system which is use in the polymerization of olefins.

DETAILED DESCRIPTION OF THE INVENTION

The first metallocene employed in producing the inventive polynuclear metallocene has the above formula wherein each Cp is a cyclopentadienyl-containing group, examples of which include substituted or unsubstituted forms of cyclopentadienyl, indenyl, tetrahydroindenyl, fluorenyl, benzofluorenyl, and the like. The substituents if present can take essentially any form that does not interfere with the desired reaction with the second metallocene. Typically the substituents on the Cp's, if present, are hydrocarbyl or hydrocarbyloxy radicals, generally containing 1 to 20 carbon atoms. The first metallocene can be an unbridged or a bridged metallocene, i.e. x can be 0 or 1. The currently preferred Me's are Zr, Hf, and Ti. When R' is organo, it is currently preferred that it be selected from the group consisting of alkyl radicals, aryl radicals, and alkoxy radicals, most preferably containing 1 to 20 carbon atoms.

A simple example of a metallocene useful as the first metallocene is the metallocene that has been come to be known as the Schwartz reagent, i.e. bis(cyclopentadienyl) zirconium hydrochloride. Techniques for preparing that metallocene and other related metallocenes that can be used as the first metallocene under the present invention are disclosed in U.S. Pat. No. 4,147,709, the disclosure of which is incorporated herein by reference. Thus the first metallocene can be selected from any of those metallocenes falling within the scope of the formula set forth in lines 20–25 of column 2 of U.S. Pat. No. 4,147,709. Metallocenes useful as the first metallocene which contain hydrocarbyl R' groups can be prepared by reacting a compound of the formula

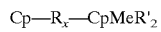

with a suitable hydrogenation agent.

A wide range of metallocenes are considered to be useful as the second metallocene employed in the present invention. The essential feature is that the second metallocene be one wherein at least one cyclopentadienyl ligand has a substituent having an olefinic or acetylenic function. The second metallocene can thus also be either a bridged and unbridged metallocenes. The unbridged metallocenes can even include bridged ligands which contain two cyclopentadienyl-type radicals connected by a suitable bridging structure but wherein only one of the cyclopentadienyl-type radicals of that ligand is actually bonded to the transition metal.

The metallocenes of the type contemplated as useful for the use as the second metallocene in the present invention include bridged metallocenes represented by the formulas R(Z)(Z)MeQ$_k$ and unbridged metallocenes of the formula (Z)(Z) MeQ$_k$ wherein each Z is bound to Me and is the same or different and is a cyclopentadienyl-type ligand selected from substituted or unsubstituted cyclopentadienyl, indenyl, tetrahydroindenyl, octahydrofluorenyl, benzofluorenyl, and fluorenyl ligands; R is a structural bridge linking the Z's; Me is a metal selected from the group consisting of IVB, VB, and VIB metals of the Periodic Table; each Q is the same or different and is selected from the group consisting of hydrogen, halogens, and organoradicals; and k is a number sufficient to fill out the remaining valances of Me, with the further proviso at least one of said Z's or R has at least one olefinic or acetylenic substituent attached to it. Thus in bridged metallocenes this unsaturated substituent can be a branch on the bridging unit R and/or on one or both of the cyclopentadienyl-type groups of the bridged ligands.

The present invention thus envisions using bridged metallocenes wherein R is a divalent radical selected from the group consisting of alkylene radicals, diorgano divalent radicals of Si, Ge, and Sn, and divalent organo radicals of P and N. If R is a divalent radical of Si, Ge, Sn, P, or N the other valences are preferably attached to hydrocarbyl groups. Generally R has 1 to 30 carbon atoms exclusive of any unsaturated branch. If R is alkylene it preferably contains about 1 to 15 carbon atoms exclusive of any unsaturated branch.

The term acetylenic substituent is used herein to include substituents of the formula

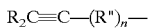

where R' is hydrogen or an organo group, n is 1 or 0, and R" is an organo group. The number of carbon atoms in the organo groups R' and R" can vary over a wide range, but generally would be in the range of about 1 to about 20, more typically about 1 to about 10. In the currently preferred embodiments R' is hydrocarbyl, preferably alkyl or aryl.

The term olefinic substituent is used herein to include substituents of the formula

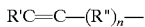

where each R' is the same or different and is selected from hydrogen and organo radicals, n is 1 or 0, and R" is a divalent organo radical. The number of carbon atoms in the organo groups R' and R" can vary over a wide range, but generally would be in the range of about 1 to about 20, more typically about 1 to about 10. In the currently preferred embodiments R' if organo is hydrocarbyl, preferably alkyl or aryl.

Various techniques are known in the art for producing various ligands having alkynyl substitution. For example EPO 577,581 discloses preparing 2,7-di(t-butylethynyl) fluorene by reacting 2,7-di(iodo)fluorene with t-butyl acetylene in the presence of an organopalladium catalyst. Such techniques are described in J. Org. Chem. 48, 1854–1862 (1983). Similarly *Izv. Akad. Nauk SSSR, Ser. Khim.* 1975,(2), 441–442 discloses the preparation of 2,7-di(phenylethynyl) fluorene by the reaction of 2,7-di(iodo)fluorene with copper phenylacetylide. Branched bridged ligands useful for making metallocenes suitable for the present invention can also be prepared by reacting a dihalo compound having an alkynyl substituent branch with an alkali metal salt of a suitable cyclopentadiene-type compound to produce a compound of the formula Z—R—Z where R is a bridge having a branch having an alkynyl substituent and wherein each Z is the same or alternatively to first produce a compound of the formula Z—R—X wherein X is a halogen and then reacting that compound with an alkali metal salt of another different cyclopentadiene-type compound to produce a compound of the formula Z—R—Z wherein the two Z's differ. Such reactions can be carried out using conditions of the type disclosed in U.S. Pat. No. 5,191,132.

An alternate technique for forming a bridged ligand having alkynyl substituents involves reacting a carbonyl compound having olefinic unsaturation with cyclopentadiene in the presence of pyrrolidine and methanol to yield an alkenyl fulvene which is then reacted with an alkali metal salt of a cyclopentadiene compound having at least one internal alkynyl substituent, such as, for example, 2,7-di (phenylethynyl) fluorene, to yield the unsaturated-branched-bridged ligand containing two cyclopentadienyl-type groups, i.e. fluorenyl and cyclopentadienyl. For example, one could react 5-hexene-2-one with cyclopentadiene using a procedure like that disclosed by Stone et al in *J. Org. Chem.* 49, 1849 (1984) to yield 6-(3-butenyl)-6-methylfulvene which could then be reacted with 2,7-di (phenylethynyl) fluorenyl lithium and subsequently hydrolyzed to yield 5-cyclopentadienyl-5-(2,7-di(phenylethynyl) fluorenyl)-1-hexene. Such a procedure results in a ligand having both olefinic and alkynyl substituents.

The metallocenes of ligands containing the required olefinic or aceylenic substituents can be prepared by reacting the ligand with an alkali metal alkyl to produce a ligand salt that is then reacted with the transition metal compound to yield the metallocene, using the techniques generally known in the art for forming such metallocenes. See, for example, the technique disclosed in European Published Application 524,624, the disclosure of which is incorporated herein by reference.

Some typical examples of what is meant by metallocenes containing an alkynyl substituent as required by the present invention include 5-(cyclopentadienyl)-5-(2,7-di(2-phenylethynyl)fluorenyl)-1-hexene zirconium dichloride which could also be named
1-(cyclopentadienyl)-1-(2,7-di(2-phenylethynyl)fluorenyl)-1-(methyl)-1-(but-3-enyl methane zirconium dichloride,
(2,7-di(phenylethynyl)fluorenyl) (cyclopentadienyl) zirconium dichloride,
(2,7-di(phenylethynyl)fluorenyl) (cyclopentadienyl) hafnium dichloride,
(2,7-di(t-butylethynyl)fluorenyl) (cyclopentadienyl) zirconium dichloride,
(2,7-di(t-butylethynyl)fluorenyl) (cyclopentadienyl) hafnium dichloride,
((phenylethynyl)cyclopentadienyl)(cyclopentadienyl) zirconium dichloride,
((t-butylethynyl) cyclopentadienyl)(cyclopentadienyl) zirconium dichloride,
(2,7-di(n-butylethynyl)fluorenyl) (cyclopentadienyl) zirconium dichloride,
(2,7-di(n-butylethynyl)fluorenyl) (cyclopentadienyl) hafnium dichloride,
(2,7-di(methylethynyl)fluorenyl) (cyclopentadienyl) zirconium dichloride,
(2,7-di(methylethynyl)fluorenyl) (cyclopentadienyl) hafnium dichloride,
1,2-bis-(2,7-di(n-butylethynyl)fluorenyl) ethane zirconium dichloride,
1,2-bis-(2,7-di(n-butylethynyl)fluorenyl) ethane hafnium dichloride,
1,2-bis-(2,7-di(phenylethynyl)fluorenyl) ethane zirconium dichloride,
1,2-bis-(2,7-di(t-butylethynyl)fluorenyl) ethane zirconium dichloride,
1-(2,7-di(n-butylethynyl)fluorenyl) 1-(cyclopentadienyl)-1,1-di(methyl) methane zirconium dichloride,
1-(2-(n-butylethynyl)fluorenyl)-1-(cyclopentadienyl)-1,1-di (methyl) methane zirconium dichloride,
1-(indenyl)-1-(cyclopentadienyl)-1-(methyl)-1-(n-butylethynyl) methane zirconium dichloride,
1-(fluorenyl)-1-(cyclopentadienyl)-1-(methyl)-1-(methylethynyl) methane zirconium dichloride,
1-(fluorenyl)-1-(cyclopentadienyl)-1-(methyl)-1-(phenylethynyl) methane zirconium dichloride, 1-(fluorenyl)-1-(cyclopentadienyl)-1-(methyl)-1-(n-butylethynyl) methane zirconium dichloride,
1-(fluorenyl)-1-(cyclopentadienyl)-1-(methyl)-1-(t-butylethynyl) methane zirconium dichloride,
1-(2,7-di(n-butylethynyl)fluorenyl)-2-(indenyl) ethane zirconium dichloride,
1-(3-(n-butylethynyl)fluorenyl)-2-(indenyl) ethane zirconium,
bis(9-fluorenyl)(methyl)(phenylethynyl)silane zirconium dichloride,
(cyclopentadienyl)(indenyl) (methyl)(phenylethynyl)silane zirconium dichloride,
(cyclopentadienyl)(9-fluorenyl) (methyl)(methylethynyl) silane zirconium dichloride, and the like.

Examples of bridged bis-indenyl metallocenes having alkynyl groups are also suggested in U.S. Pat. No. 5,391,790. Such metallocenes are within the scope required by the present invention when the alkynyl groups are internal alkynyl.

The term fluorenyl as used herein refers to 9-fluorenyl unless specifically indicated as otherwise. Accordingly, the term fluorenyl and 9-fluorenyl should be viewed as equivalent unless something indicates otherwise.

Some typical examples of some metallocenes containing a substituent having olefinic unsaturation include
5-(cyclopentadienyl)-5-(9-fluorenyl)-1-hexene zirconium dichloride,
bis(9-fluorenyl)(methyl)(vinyl)silane zirconium dichloride,
bis(9-fluorenyl)(methyl)(propenyl)silane zirconium dichloride,
bis(9-fluorenyl) (methyl)(butenyl)silane zirconium dichloride,
bis(9-fluorenyl) (methyl)(hexenyl)silane zirconium dichloride,
bis(9-fluorenyl)(methyl)(octenyl)silane zirconium dichloride,
(cyclopentadienyl)(propenylindenyl) zirconium dichloride,
bis(1-propenylindenyl) zirconium dichloride,
(9-propenylfluorenyl)(cyclopentadienyl) zirconium dichloride,
(9-propenylfluorenyl)(pentamethylcyclopentadienyl) zirconium dichloride,
bis(9-propenylfluorenyl) zirconium dichloride,
(9-cyclopentenylfluorenyl)(cyclopentadienyl) zirconium dichloride,
bis(9-cyclopentenylfluorenyl) zirconium dichloride,
5-(methylcyclopentadienyl)-5-(9-fluorenyl)-1-hexene zirconium dichloride,
5-(fluorenyl)-5-(cyclopentadienyl)-1-hexene hafnium dichloride,
(fluorenyl)(propenylindenyl)dimethylsilane zirconium dichloride,
1-(2,7-di(alpha-methylvinyl)fluorenyl)-1-(cyclopentadienyl)-1,1-dimethylmethane zirconium dichloride,
1-(2,7-di(cyclohex-1-enyl) fluorenyl)-1-(cyclopentadienyl)-1,1-methane zirconium dichloride, and the like.

The first and second metallocenes can be reacted together under a wide range of reaction conditions. Generally, however, they would be reacted together in a liquid diluent which is preferably a solvent for at least one of the two metallocenes. The molar ratio of the first and second metallocenes can vary over a wide range. Typically however about one mole of the first metallocene is used for each reactive olefinic or acetylenic substituent on the second metallocene. The temperature employed in the reaction can also vary over a wide range. Typically however the reaction would be carried out at a temperature in the range of about 0° C. to about 100° C. Generally mixing for a few hours at normal room temperature, i.e. about 15° to 25° C., is sufficient to effect the reaction. The resulting polynuclear metallocene can then be recovered from the reaction mixture and purified using conventional procedures.

The resulting polynuclear metallocene can be used for the polymerization. The inventive catalyst systems are particularly useful for the polymerization of alpha-olefins having 2 to 10 carbon atoms. Examples of such olefins include ethylene, propylene, butene-1, pentane-1, 3-methylbutene-1, hexene-1, 4-methylpentene-1, 3-methylpentene-1, heptene-1, octene-1, decene-1, 4,4-dimethyl-1-pentane, 4,4-diethyl-1-hexene, 3,4-dimethyl-1-hexene, and the like and mixtures thereof. The catalysts are also useful for preparing copolymers of ethylene and propylene and copolymers of ethylene or propylene and a higher molecular weight olefin. Monomers such as styrene and butadiene are also useful.

Polymerizations with the inventive catalyst can be carried out under a wide range of conditions depending upon the particular metallocene employed and the particular results desired. The inventive catalyst systems are considered useful for polymerization conducted under solution, slurry, or gas phase reaction conditions. Typically the inventive metallocene would be used with a suitable cocatalyst.

Examples of suitable cocatalysts include generally any of those organometallic cocatalysts which have in the past been employed in conjunction with transition metal containing olefin polymerization catalysts. Some typical examples include organometallic compounds of metals of Groups IA, IIA, and IIIB of the Periodic Table. Examples of such compounds have included organometallic halide compounds, organometallic hydrides and even metal hydrides. Some specific examples include triethylaluminum, triisobutylaluminum, diethylaluminum chloride, diethylaluminum hydride, and the like. Other examples of known cocatalysts include the use of a stable non-coordinating counter anion cocatalyst, an example of such is disclosed in U.S. Pat. No. 5,155,080, e.g. using triphenyl carbenium tetrakis (pentafluorophenyl) boronate. Another example would be the use a mixture of trimethylaluminum and dimethylfluoroaluminum such as disclosed by Zambelli et, *Macromolecules* 22, 2186 (1989). In such counter anion systems the cocatalyst can be viewed as an ion-exchange compound comprising a cation which will irreversibly react with as least one ligand contained in the metallocene and a non-coordination anion which is ether a single coordination complex comprising a plurality of lipophilic radicals covalently coordinated to and shielding a central formally charge-bearing metal or metalloid atom or an anion comprising a plurality of boron atoms such as polyhedral boranes, carboranes, and metallacarboranes.

The currently most preferred cocatalyst is an aluminoxane. Such compounds include those compounds having repeating units of the formula

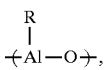

where R is generally a hydrocarbyl group having 1 to 5 carbon atoms. The organo aluminoxane component used in preparing the inventive solid catalyst system include oligomeric aluminum compounds having repeating units of the formula

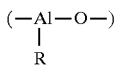

Some examples are often represented by the general formula (R—Al—O)$_n$ or R(R—Al—O—)$_n$AlR$^2$. In the general aluminoxane formula R is preferably a C$_1$–C$_5$ alkyl radical, for example, methyl, ethyl, propyl, butyl or pentyl and "n" is an integer from 1 to about 50. Most preferably, R is methyl and "n" is at least 4.

Aluminoxanes can be prepared by various procedures known in the art. For example, an aluminum alkyl may be treated with water dissolved in an inert organic solvent, or it may be contacted with a hydrated salt, such as hydrated copper sulfate suspended in an inert organic solvent, to yield an aluminoxane. Generally the reaction of an aluminum alkyl with a limited amount of water is postulated to yield a mixture of the linear and cyclic species of the aluminoxane. Aluminoxanes, also sometimes referred to as poly (hydrocarbyl aluminum oxides) are well known in the art and are generally prepared by reacting an hydrocarbylaluminum compound with water. Such a preparation techniques are disclosed in U.S. Pat. Nos. 3,242,099 and 4,808,561, the disclosures of which are incorporated herein by reference. The currently preferred aluminoxane cocatalysts are prepared either from trimethylaluminum or triethylaluminum and are sometimes referred to as poly(methyl aluminum oxide) and poly(ethyl aluminum oxide), respectively. It is also within the scope of the invention to use an aluminoxane in combination with a trialkylaluminum, such as disclosed in U.S. Pat. No. 4,794,096, the disclosure of which is incorporated herein by reference.

In a particular preferred embodiment, the polynuclear metallocene can be employed in combination with a solid organoaluminoxane which is substantially insoluble in the polymerization diluent under particle form polymerization conditions. Such a solid aluminoxane can be prepared by contacting a solution of an organoaluminoxane with an organoboroxine under conditions sufficient to produce a solid. Another technique for preparing an insoluble organoaluminoxane involves contacting a solution of an organoaluminoxane with water or an active hydrogen compound as taught in U.S. Pat. No. 4,990,640.

Still another technique of producing a solid cocatalyst involves contacting an organoaluminoxane with an organic borane compound free of acidic hydrogen as taught U.S. Pat. No. 5,354,721, the disclosure of which is incorporated herein by reference. Yet another technique involves contacting an organoaluminoxane with an organoboron compound having boron acid functionality, i.e. —BOH, as taught in U.S. Pat. No. 5,414,189, the disclosure of which is incorporated herein by reference.

The currently preferred technique for preparing the solid organoaluminoxy cocatalyst involves contacting an organic solution of an organoaluminoxane optionally containing trialkylaluminums with a suitable organoboroxine compound as taught in U.S. Pat. No. 5,411,925, the disclosure of which is incorporated herein by reference.

When the polymerizations are carried out in the presence of liquid diluents obviously it is important to use diluents which do not have an adverse effect upon the catalyst system. Typical liquid diluents include propane, butane, isobutane, pentane, hexane, heptane, octane, cyclohexane, methylcyclohexane, toluene, xylene, and the like. Typically the polymerization temperature can vary over a wide range, temperatures typically would be in a range of about −60° C. to about 300° C., more preferably in the range of about 20° C. to about 160° C. Typically the pressure of the polymerization would be in the range of from about 1 to about 500 atmospheres or even greater. The inventive catalyst system is particularly useful for polymerizations carried out under particle form, i.e., slurry-type polymerization conditions.

In a particularly preferred embodiment of the present invention the polynuclear metallocene is subjected to prepolymerization with an olefin to produce a solid catalyst system that can later be used in the polymerization of olefins. This technique is particularly useful in slurry or particle-form type polymerizations.

To prepare the solid prepolymerized catalyst system the metallocene and aluminoxane are combined in the presence of a suitable liquid to form a liquid catalyst system. It is preferred that the liquid catalyst system be prepared using an organic liquid in which the aluminoxane is at least partially soluble. The currently preferred liquids are hydrocarbons such as hexane or toluene. Typically an aromatic liquid solvent is employed. Examples include benzene, toluene, ethylbenzene, diethylbenzene, and the like. The amount of liquid to be employed is not particularly critical. Nevertheless, the amount should preferably be such as to dissolve at least a portion of the product of the reaction between the metallocene and the aluminoxane, provide desirable polymerization viscosity for the prepolymerization, and to permit good mixing. The temperature is preferably kept below that which would cause the metallocene to decompose. Typically the temperature would be in the range of −50° C. to 100° C. Preferably, the metallocene, the aluminoxane, and the liquid diluent are combined at room temperature, i.e. around 10° to 30° C. The reaction between the aluminoxane and the metallocene is relatively rapid. The reaction rate can vary depending upon the ligands of the metallocene. It is generally desired that they be contacted for at least about a minute to about 1 hour.

It is within the scope of the invention to form the liquid catalyst system in the presence of a particulate solid. Any number of particulate solids can be employed as the particulate solid. Typically the support can be any organic or inorganic solid that does not interfere with the desired end result. Examples include porous supports such as talc, inorganic oxides, and resinous support materials such as particulate polyolefins. Examples of inorganic oxide materials include Groups II, III, IV or V metal oxides such as silica, alumina, silica-alumina, and mixtures thereof. Other examples of inorganic oxides are magnesia, titania, zirconia, and the like. Other suitable support materials which can be employed include materials such as, magnesium dichloride, and finely divided polyolefins, such as polyethylene. It is within the scope of the present invention to use a mixture of one or more of the particulate solids.

It is generally desirable for the solid to be thoroughly dehydrated prior to use, preferably it is dehydrated so as to contain less than 1% loss on ignition. Thermal dehydration treatment may be carried out in vacuum or while purging with a dry inert gas such as nitrogen at a temperature of about 20° C. to about 1000° C., and preferably, from about 300° C. to about 800° C. Pressure considerations are not critical. The duration of thermal treatment can be from about 1 to about 24 hours. However, shorter or longer times can be employed provided equilibrium is established with the surface hydroxyl groups.

Dehydration can also be accomplished by subjecting the solid to a chemical treatment in order to remove water and reduce the concentration of surface hydroxyl groups. Chemical treatment is generally capable of converting all water and hydroxyl groups in the oxide surface to relatively inert species. Useful chemical agents are for example, trimethylaluminum, ethyl magnesium chloride, chlorosilanes such as $SiCl_4$, disilazane, trimethylchlorosilane, dimethylaminotrimethylsilane and the like.

The chemical dehydration can be accomplished by slurrying the inorganic particulate material such as, for example silica, in an inert low boiling hydrocarbon, such as for example, hexane. During the chemical dehydration treatment, the silica should be maintained in a moisture and oxygen free atmosphere. To the silica slurry is then added a low boiling inert hydrocarbon solution of the chemical dehydrating agent, such as, for example dichloroldimethylsilane. The solution is added slowly to the slurry. The temperature ranges during chemical dehydration reaction can be from about 20° C. to about 120° C., however, higher and lower temperatures can be employed. Preferably, the temperature will be about 50° C. to about 100° C. The chemical dehydration procedure should be allowed to proceed until all the substantially reactive groups are removed from the particulate support material as indicated by cessation of gas evolution. Normally, the chemical dehydration reaction will be allowed to proceed from about 30 minutes to about 16 hours, preferably, 1 to 5 hours. Upon completion of the chemical dehydration, the solid particulate material may be filtered under a nitrogen atmosphere and washed one or more times with a dry, oxygen free inert solvent. The wash solvents as well as the diluents employed to form the slurry and the solution of chemical dehydrating agent, can be any suitable inert hydrocarbon. Illustrative of such hydrocarbons are pentane, heptane, hexane, toluene, isopentane and the like.

Another chemical treatment that can be used on solid inorganic oxides such as silica involves reduction by contacting the solid with carbon monoxide at an elevated temperature sufficient to convert substantially all the water and hydroxyl groups to relatively inactive species.

The specific particle size of the support or inorganic oxide, surface area, pore volume, and number of hydroxyl groups is not considered critical to its utility in the practice of this invention. However, such characteristics often determine the amount of support to be employed in preparing the catalyst compositions, as well as affecting the particle morphology of polymers formed. The characteristics of the carrier or support must therefore be taken into consideration in choosing the same for use in the particular invention.

It is also within the scope of the present invention to add such a particulate solid to the liquid catalyst system after it has been formed and to carry out the prepolymerization in the presence of that solid.

The amount of aluminoxane and metallocene used in forming the liquid catalyst system for the prepolymerization can vary over a wide range. Typically, however, the molar ratio of aluminum in the aluminoxane to transition metal of the metallocene is in the range of about 1:1 to about 20,000:1, more preferably, a molar ratio of about 50:1 to about 2000:1 is used. If a particulate solid, i.e. silica, is used generally it is used in an amount such that the weight ratio of the metallocene to the particulate solid is in the range of about 0.00001/1 to 1/1, more preferably 0.0005/1 to 0.2/1.

The prepolymerization is conducted in the liquid catalyst system, which can be a solution, a slurry, or a gel in a liquid. A wide range of olefins can be used for the prepolymerization. Typically, the prepolymerization will be conducted using an olefin, preferably selected from ethylene and non-aromatic alpha-olefins, and as propylene. It is within the scope of the invention to use a mixture of olefins, for example, ethylene and a higher alpha olefin can be used for the prepolymerization. The use of, a higher alpha olefin, such as 1-butene, with ethylene is believed to increase the amount of copolymerization occurring between the olefin monomer and the olefinically unsaturated portion of the metallocene.

The prepolymerization can be conducted under relatively mild conditions. Typically, this would involve using low pressures of the olefin and relatively low temperatures designed to prevent site decomposition resulting from high concentrations of localized heat. The prepolymerization typically occurs at temperatures in the range of about −30° C. to about +110° C., more preferably in the range of about +10° to about +30° C. The amount of prepolymer can be varied but typically would be in the range of from about 1 to about 95 wt % of the resulting prepolymerized solid catalyst system, more preferably about 5 to 80 wt %. It is generally desirable to carry out the prepolymerization to at least a point where substantially all of the metallocene is in the solid rather than in the liquid since that maximizes the use of the metallocene.

After the prepolymerization, the resulting solid prepolymerized catalyst is preferably separated from the liquid of the reaction mixture. Various techniques known in the art can be used for carrying out this step. For example, the material could be separated by filtration, decantation, or by vacuum evaporation. It is currently preferred, however, not to rely upon vacuum evaporation since it is considered desirable to remove substantially all of the soluble components in the liquid reaction product of the prepolymerization from the resulting solid prepolymerized catalyst before it is stored or used for subsequent polymerization. After separating the solid from the liquid, the resulting solid is preferably washed with a hydrocarbon and then dried using high vacuum to remove substantially all the liquids and other volatile components that might still be associated with the solid. The vacuum drying is preferably carried out under relatively mild conditions, i.e. temperatures below 100° C. More typically the prepolymerized solid is dried by subjection to a high vacuum at a temperature of about 30° C. until a substantially constant weight is achieved. A preferred technique employs at least one initial wash with an aromatic hydrocarbon, such as toluene, followed by a wash with a paraffinic hydrocarbon, such as hexane, and then vacuum drying.

It is within the scope of the present invention to contact the prepolymerization reaction mixture product with a liquid in which the prepolymer is sparingly soluble, i.e. a counter solvent for the prepolymer, to help cause soluble prepolymer to precipitate from the solution. Such a liquid is also useful for the subsequent washing of the prepolymerized solid.

It is also within the scope of the present invention to add a particulate solid of the type aforementioned after the prepolymerization. Thus one can add the solid to the liquid prepolymerization product before the counter solvent is added. In this manner soluble prepolymer tends to precipitate onto the surface of the solid to aid in the recovery of the filtrate in a particulate form and to prevent agglomeration during drying. The liquid mixture resulting from the prepolymerization or the inventive solid prepolymerized catalyst can be subjected to sonification to help break up particles if desired.

Further, if desired the recovered solid prepolymerized catalyst system can be screened to give particles having sizes that meet the particular needs for a particular type of polymerization.

Another option is to combine the recovered inventive solid prepolymerized catalyst system with an inert hydrocarbon, such as one of the type used as a wash liquid, and then to remove that liquid using a vacuum. In such a process it is sometimes desirable to subject the resulting mixture to sonification before stripping off the liquid.

During the prepolymerization, it is believed that at least some of the first metallocene is reformed as a result of beta-hydride chain termination during the polymerization. For many applications it may be desirable to remove this regenerated first metallocene from the solid catalyst system. Such can be accomplished by thorough washing of the solid with a solvent for the first metallocene.

The solid prepolymerized catalyst system is suitable for use in the polymerization of olefinically unsaturated monomers. Such polymerizations can be carried out under gas phase, solution phase, or slurry phase conditions. The conditions used are as conventional. One difference is that generally it is not necessary to employ an additional cocatalyst with the solid prepolymerized catalyst.

In some cases it may be found desirable to employ small amounts of an organoaluminum compound as a scavenger for poisons. The term organoaluminum compounds include compounds such as triethylaluminum, trimethylaluminum, diethylaluminum chloride, ethylaluminum dichloride, ethylaluminum sesquichloride, and the like. Trialkylaluminum compounds are currently preferred. Also in some applications it may be desirable to employ small amounts of antistatic agents which assist in preventing the agglomeration of polymer particles during polymerization. Still further, when the inventive catalyst system is added to a reactor as a slurry in a liquid, it is sometimes desirable to add a particulate dried solid as a flow aid for the slurry. Preferably the solid has been dried using one of the methods described earlier. Inorganic oxides such as silica are particularly preferred. Currently, it is preferred to use a fumed silica such as that sold under the trade name Cab-o-sil. Generally the fumed silica is dried using heat and trimethylaluminum.

The polymers produced with the catalysts herein disclosed have a wide range of uses that will be apparent to those skilled in the art from the physical properties of the respective polymers. Applications such as molding, films, adhesives, and the like are indicated.

A further understanding of the present invention, its various aspects, objects and advantages will be provided by the following examples.

EXAMPLE I

In this synthesis 20.6 mL of cyclopentadiene and 11.7 mL of 5-hexene-2-one were dissolved in 100 mL of methanol. While cooling in ice 12.4 mL of pyrrolidine was added and the reaction mixture was stirred overnight at room temperature. Then 9.6 mL of glacial acidic acid was added. The reaction mixture was stirred for one half hour and then the solvent was evaporated in a vacuum. The residue was dissolved in 200 mL of diethyl ether and washed five times with 100 mL of water. The organic phase was filtered using a silica gel and dried over sodium sulfate. The solvent was evaporated in a vacuum. A yellow oil was recovered which was identified as 6-(3-butenyl)-6-methylfulvene.

A solution was prepared by dissolving 10 g of fluorene in 100 mL of THF and then this was slowly reacted with 37.6 mL of a 1.6 molar solution of n-butyllithium in hexane. This dark red solution was stirred overnight at room temperature. Then a solution was prepared by combining 8.8 g of 6-(butenyl)-6-methylfulvene with 50 mL of THF. This solution was then added dropwise over a period of one half hour to the solution of the fluorenyl lithium salt. That reaction mixture was stirred overnight at room temperature and then 100 mL of water was added. The organic phase was dried overnight over sodium sulfate and the solvent was evaporated in a vacuum. The yellow residue was dissolved in pentane and filtered using silica gel. The solvent was concentrated by means of evaporation. Crystallization took place at about −18° C. to give 5-(cyclopentadienyl)-5-(9-fluorenyl)-1-hexene in the form of a white solid. This compound is also sometimes referred to as 1-(9-fluorenyl)-1-(cyclopentadienyl)-1-(but-3-enyl)-1-(methyl) methane.

EXAMPLE II

Five grams of 5-(cyclopentadienyl)-5-(9-fluorenyl)-1-hexene was reacted with twice as many moles of n-butyllithium in 100 mL of diethylether using conditions of the type taught in published European Patent Application 524,624 to produce the divalent ligand salt. The divalent ligand salt was then reacted with 3.96 grams of zirconium tetrachloride at room temperature. The orange metallocene 5-(9-fluoreny)-5-(cyclopentadienyl)-1-hexene zirconium dichloride was recovered and purified by decanting off the liquid and recrystallizing in dichloroethane at −18° C. The liquid was decanted off and the solid dried using a high vacuum.

EXAMPLE III

A binuclear metallocene was prepared by suspending 2.85 grams of 5-(cyclopentadienyl)-5-(9-fluorenyl)-1-hexene zirconium dichloride and 1.6 grams of bis(cyclopentadienyl) zirconium hydrochloride, i.e. zirconcene hydridochloride, in 50 mL of tetrahydrofuran and stirred overnight at room temperature. The liquid was then evaporated in a vacuum and the residue was extracted over sodium sulfate using methylene chloride. The n-pentane was slowly added to the extract and a solid precipitate resulted which was separated from the supernatant liquid. The resulting solid was a binuclear metallocene of the formula $Cp_2ZrCl(CH_2)_4C(CH_3)(Fl)(Cp)ZrCl_2$, wherein Fl is 9-fluorenyl and Cp is cyclopentadienyl. Such could be referred to as (4-(biscyclopentadienylzirconium chloride) butanyl)-(9-fluorenyl) (cyclopentadienyl) (methyl) methane zirconium dichloride.

EXAMPLE IV

The effectiveness of the solid binuclear metallocene of Example III as a catalyst for olefin polymerization was evaluated. The polymerization was conducted in a one gallon stirred autoclave reactor. A catalyst slurry was prepared by combining 10 mL of a 1.1M toluene solution of methylaluminoxane obtained from Schering with 0.0165 grams of the binuclear metallocene of Example III. The catalyst system was charged to the autoclave. The autoclave was filled with 2 liters of isobutane and the temperature was raised to about 90 C., the polymerization temperature. Hydrogen was added from a 300 cc autoclave in an amount equal to a pressure drop of about 15 psi and then the vessel was pressurized to 450 psig with ethylene. The polymerization was continued for one hour after reaching the 90 degree C. reaction temperature. The reactor was then cooled and vented, and the solid polymer was recovered. A solid polymer having a density of 0.9554 was recovered. The weight average molecular weight was 104,000 and the Heterogenity Index, i.e. Mw/Mn was 5, which indicates that this metallocene produced a broader molecular weight distribution than that generally produced by more simple metallocenes. The polymer had a Melt Index of 0.84 dg/min and a HLMI of 41.1 dg/min.

That which is claimed is:

1. A process for preparing a polynuclear metallocene comprising reacting a first metallocene of the formula

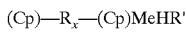

with a second metallocene, said second metallocene having at least one cyclopentadienyl-containing group having a substituent having an olefinic or acetylenic function, wherein in the above formula each Cp is the same or a different cyclopentadienyl-containing group, R is an organic moiety connecting the two Cp's; Me is a transition metal selected from metals of Groups IVB, VB, and VIB; R' is selected from the group consisting of hydrocarbyl, hydrocarbyloxy, and halides; and x is 1 or 0.

2. A process according to claim 1 wherein said second metallocene is selected from metallocenes in which at least one cyclopentadienyl-containing groups has a substituent having an olefinic function.

3. A process according to claim 1 wherein said second metallocene is selected from metallocenes in which at least one cyclopentadienyl-containing groups has a substituent having a terminal olefinic function.

4. A process according to claim 3 wherein said first metallocene is bis(cyclopentadienyl) zirconium chlorohydride.

5. A process according to claim 4 wherein said second metallocene is selected from bridged metallocenes in which the bridge has a branch having olefinic unsaturation.

6. A process according to claim 5 wherein said second metallocene contains two halide substituents bonded to the transition metal of the metallocene.

7. A process according to claim 6 wherein the metal of the second metallocene is zirconium.

8. A process according to claim 7 wherein said second metallocene is 5-(cyclopentadienyl)-5-(9-fluorenyl)-1-hexene zirconium dichloride.

9. A process according to claim 3 wherein the metal of the second metallocene is other than zirconium.

10. A process according to claim 1 wherein the metal of the second metallocene is other than zirconium.

11. A metallocene produced by the process of claim 1.

12. The metallocene produced by the process of claim 8.

13. A process for polymerizing an olefin comprising contacting said olefin under suitable polymerization conditions with a catalyst comprising a metallocene of claim 11.

14. A process according to claim 13 which produces a prepolymerized solid catalyst suitable for use in olefin polymerization which contains no more than about 95 weight percent polymer.

15. A solid prepolymerized catalyst produced by the process of claim 14.

16. A process for polymerizing an olefin comprising contacting said olefin with a catalyst comprising a solid prepolymerized catalyst of claim 15 under suitable polymerization conditions.

17. A process for polymerizing an olefin comprising contacting said olefin under suitable polymerization conditions with a catalyst comprising a metallocene of claim 12.

18. A process for producing a prepolymerized solid catalyst suitable for use in the polymerization of olefins comprising contacting an olefin under suitable polymerization conditions with a metallocene as set forth in claim 11 to produce a prepolymerized solid, separating the first metallocene from the remaining solid, and recovering the solid as said solid prepolymerized catalyst.

19. A process according to claim 2 wherein the metals of the first and second metallocenes are different.

20. A process according to claim 19 wherein the metal of the first metallocene is zirconium.

* * * * *